United States Patent
Nakanishi et al.

(10) Patent No.: US 9,234,934 B2
(45) Date of Patent: Jan. 12, 2016

(54) INSPECTING DEVICE AND INSPECTING METHOD

(71) Applicants: DAINIPPON SCREEN MFG. CO., LTD, Kyoto (JP); OSAKA UNIVERSITY, Osaka (JP)

(72) Inventors: Hidetoshi Nakanishi, Kyoto (JP); Akira Ito, Kyoto (JP); Masayoshi Tonouchi, Suita (JP); Iwao Kawayama, Suita (JP)

(73) Assignees: SCREEN HOLDINGS CO., LTD., Kyoto (JP); OSAKA UNIVERSITY, Osaka (JP)

( * ) Notice: Subject to any disclaimer, the term of this patent is extended or adjusted under 35 U.S.C. 154(b) by 210 days.

(21) Appl. No.: 13/931,729

(22) Filed: Jun. 28, 2013

(65) Prior Publication Data

US 2014/0002125 A1 Jan. 2, 2014

(30) Foreign Application Priority Data

Jun. 28, 2012 (JP) ................................ 2012-145171

(51) Int. Cl.
*G01R 31/26* (2014.01)
*G01N 21/95* (2006.01)
(Continued)

(52) U.S. Cl.
CPC ........ *G01R 31/2605* (2013.01); *G01N 21/3586* (2013.01); *G01N 21/9501* (2013.01); *G01N 21/956* (2013.01); *H02S 50/10* (2014.12)

(58) Field of Classification Search
CPC ..... H02S 50/10; H02S 50/15; G01N 21/3586; G01N 21/9501; G01N 21/956; G01R 31/26; G01R 31/2601; G01R 31/2607; G01R 31/2635; G01R 31/2637
See application file for complete search history.

(56) References Cited

U.S. PATENT DOCUMENTS 7,601,941 B2 10/2009 Fuyuki
8,129,683 B2 3/2012 Itsuji et al.
(Continued)

FOREIGN PATENT DOCUMENTS

EP 1441233 A1 7/2004
EP 2546634 A1 1/2013
(Continued)

OTHER PUBLICATIONS

Akihiko Ooi, "Technology of the Microscopic Analysis for Semiconductor Devices", Fuji Jihou, vol. 76, No. 3 (2003) pp. 197-200, with partial English Translation.
(Continued)

*Primary Examiner* — Tung X Nguyen
*Assistant Examiner* — David Frederiksen
(74) *Attorney, Agent, or Firm* — McDermott Will & Emery LLP

(57) ABSTRACT

An inspecting device serves to inspect a solar cell. The inspecting device includes an irradiation part for irradiating with pulsed light and a detection part having a detector for detecting an electromagnetic wave pulse radiated from the solar cell depending on the irradiation with the pulsed light. The detector detects an electric field intensity of the electromagnetic wave pulse depending on irradiation with probe light emitted from a light source (a femtosecond laser) of the pulsed light. Moreover, the inspecting device includes a delay part for delaying a timing for detecting the electromagnetic wave pulse in the detector. Furthermore, the inspecting device includes an electromagnetic wave pulse analysis part for detecting a negative peak of the electric field intensity in a temporal waveform of the electromagnetic wave pulse.

5 Claims, 13 Drawing Sheets

(51) Int. Cl.
  *G01N 21/956* (2006.01)
  *G01N 21/3586* (2014.01)
  *H02S 50/10* (2014.01)

(56) References Cited

U.S. PATENT DOCUMENTS

| | | | |
|---|---|---|---|
| 8,513,608 B2* | 8/2013 | Ohtake et al. | 250/341.8 |
| 2005/0098728 A1* | 5/2005 | Alfano | G01N 21/3581 250/341.8 |
| 2007/0018634 A1* | 1/2007 | Ohtake et al. | 324/96 |
| 2008/0084554 A1* | 4/2008 | Ohtake et al. | 356/51 |
| 2008/0137068 A1* | 6/2008 | Ouchi et al. | 356/51 |
| 2010/0090112 A1* | 4/2010 | Kawada | G01N 21/35 250/338.4 |
| 2010/0195092 A1* | 8/2010 | Ohtake | G01B 11/0666 356/51 |
| 2010/0231253 A1 | 9/2010 | Kitagawa et al. | |

FOREIGN PATENT DOCUMENTS

| | | |
|---|---|---|
| JP | 2009-175127 A | 8/2009 |
| WO | 2006059615 A1 | 6/2006 |
| WO | WO 2011105040 A1 * | 9/2011 |

OTHER PUBLICATIONS

European Search Report Application No. EP 13 16 7658 dated Oct. 24, 2013.
Yamashita Masatsugu et al., "Noncontact inspection technique for electrical failures in semiconductor devices using a laser terahertz emission microscope", Applied Physics Letters, AIP, American Institute of Physics, Melville, NY, US, vol. 93, No. 4, Jul. 31, 2008, pp. 41117-1-41117-3, XP012113211.

* cited by examiner

F I G. 1
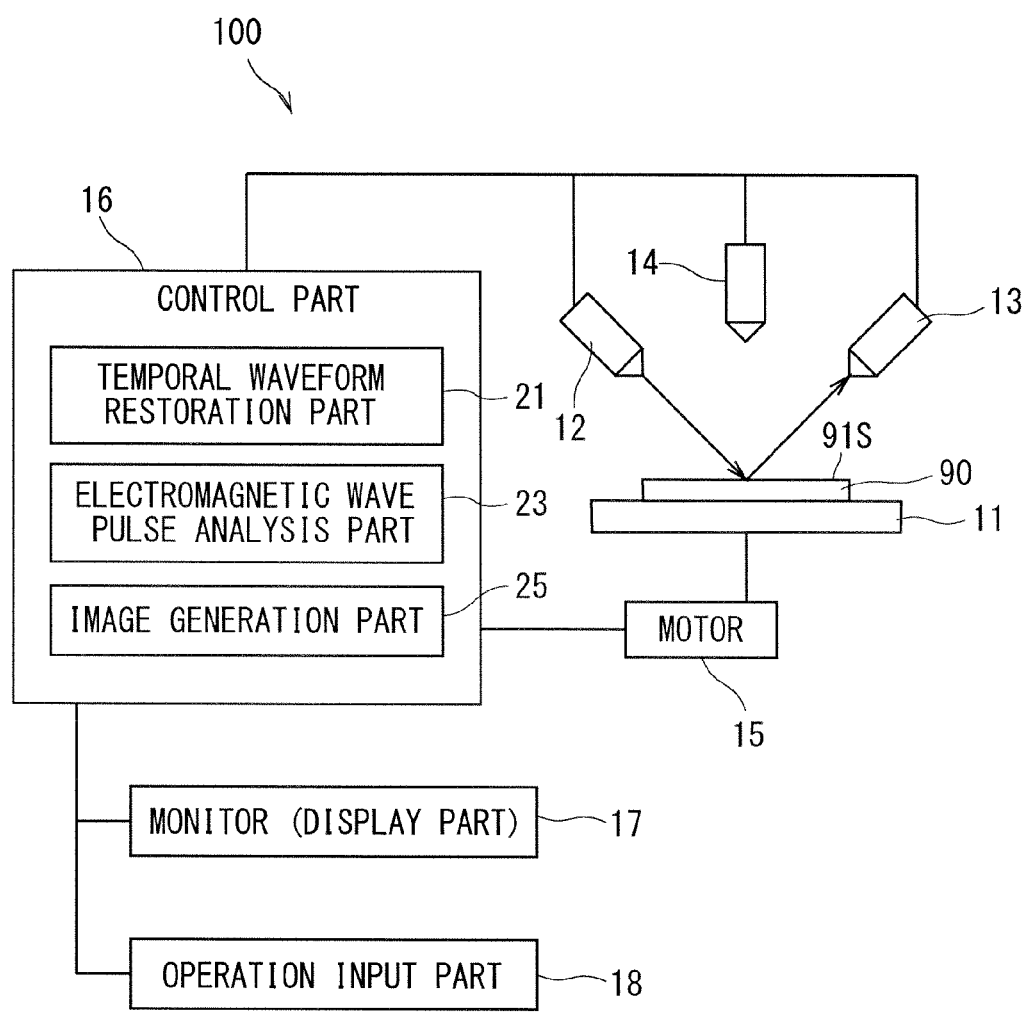

F I G. 3
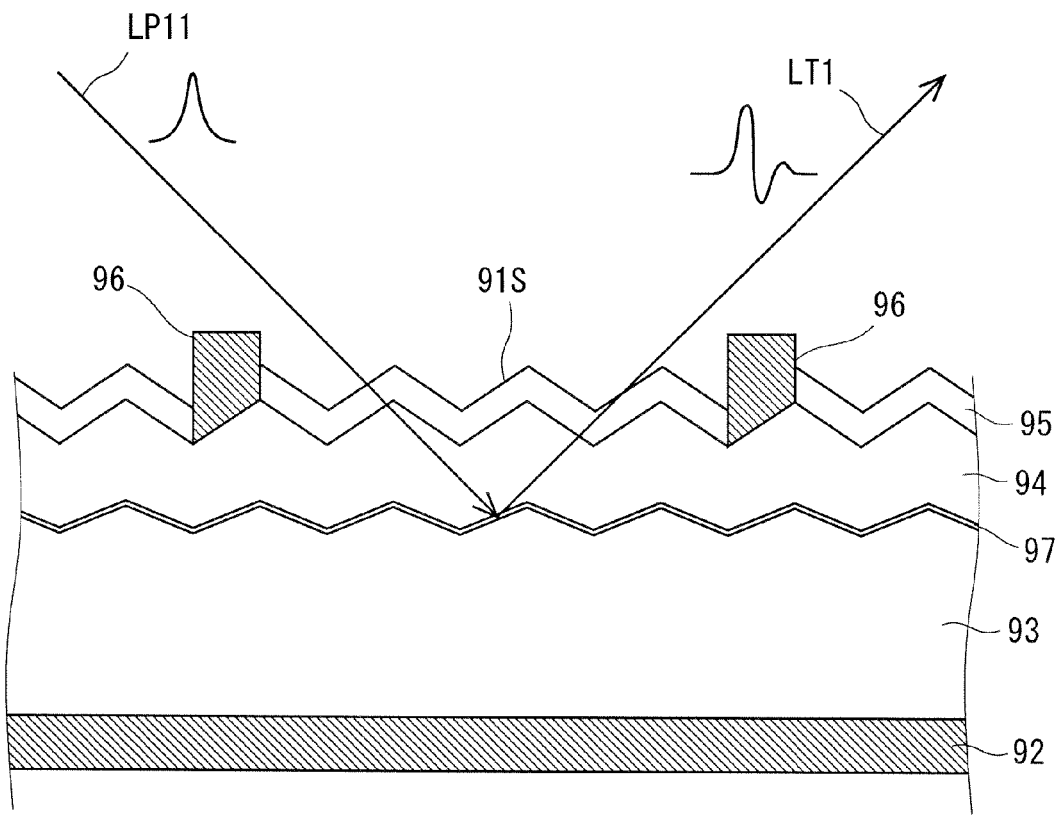

F I G. 5
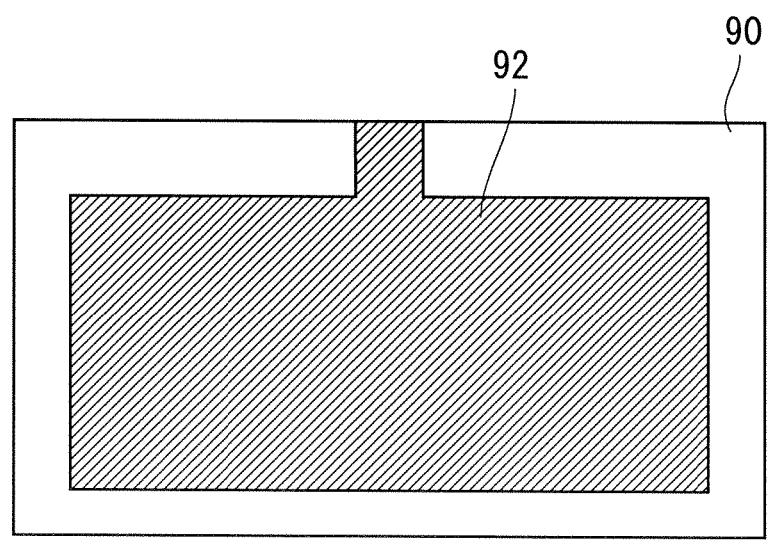

F I G. 6
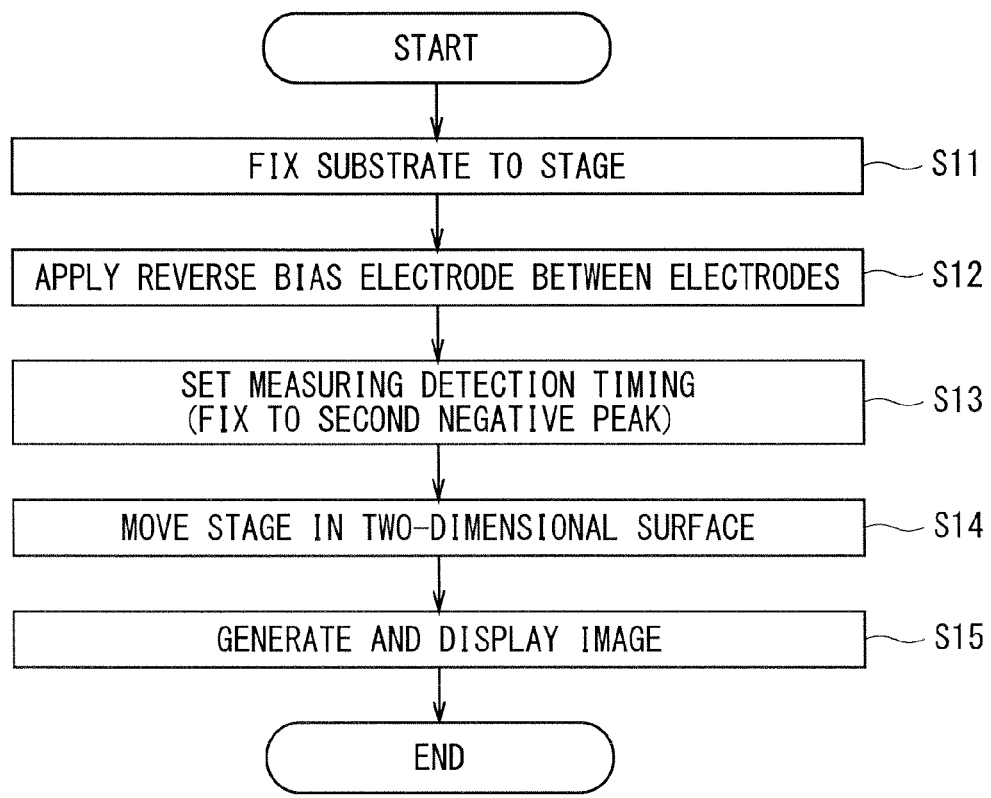

F I G. 1 1
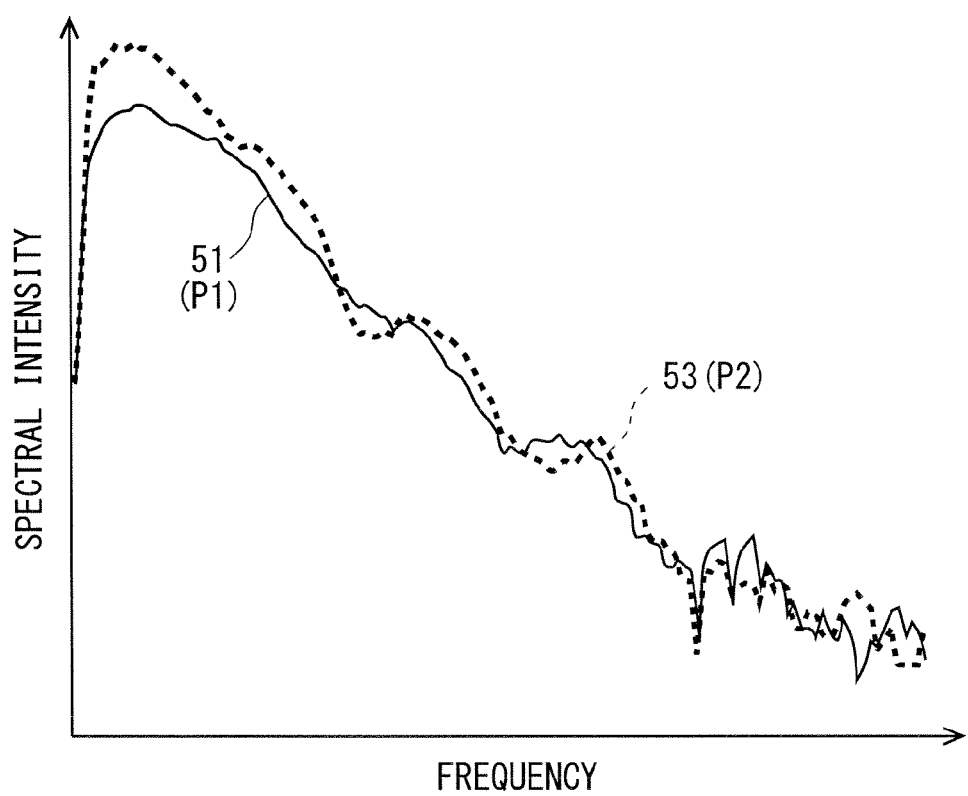

F I G. 1 2
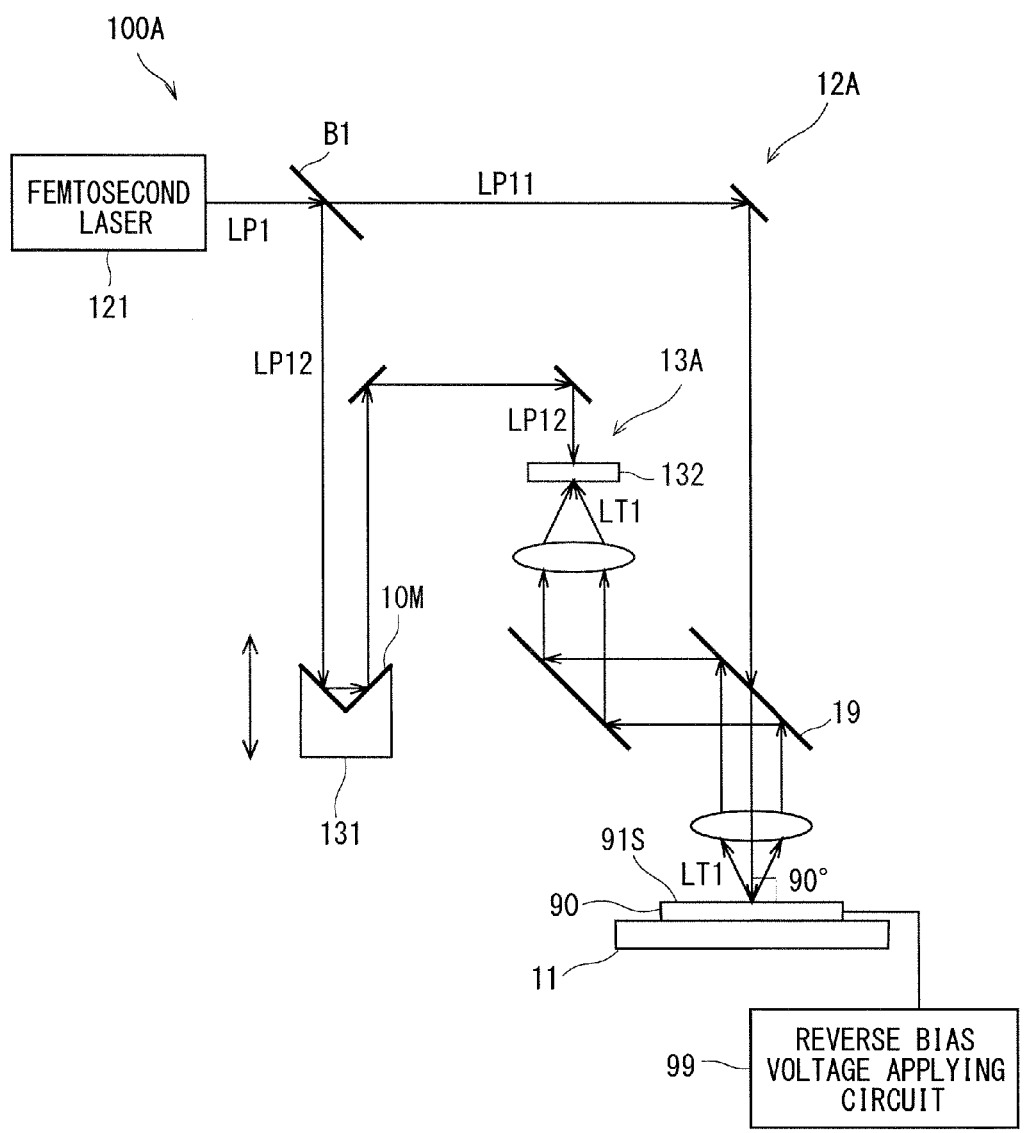

F I G. 1 3
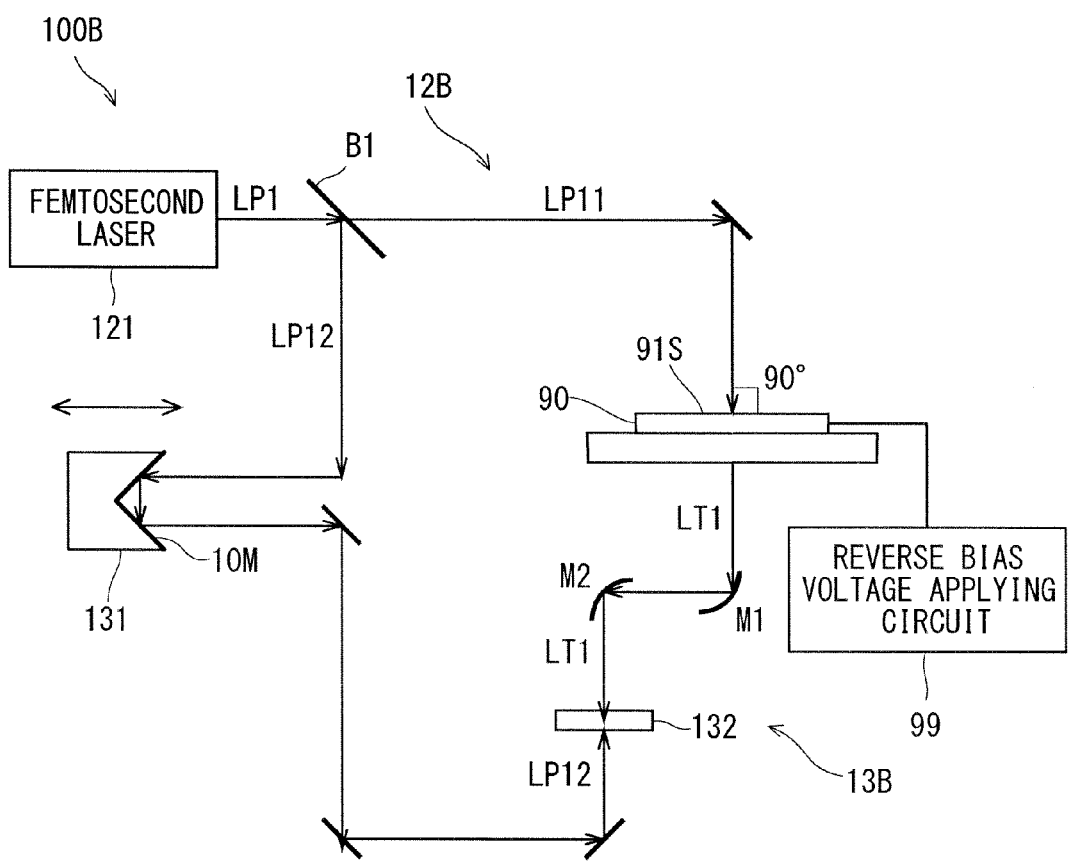

INSPECTING DEVICE AND INSPECTING METHOD

BACKGROUND OF THE INVENTION

1. Field of the Invention

The present invention relates to a technique for inspecting a photo device.

2. Description of the Background Art

A photo device utilizes photovoltaic effect, and a photodiode, an image sensor, a solar cell and the like are manufactured as products, for example.

For example, solar cells utilizing single crystal silicon and polycrystal silicon occupy a mainstream, and studies are being conducted in order to enhance power generation efficiency. Moreover, the image sensor is being studied in order to increase sensitivity, to enhance an S/N ratio and to reduce a price with a focus on the security field or the sensing field.

The photo device is an element utilizing photoexcited carriers (a free electron and a free hole) generated by irradiating a depletion layer of a PN junction body with light. By analyzing a situation in which the photoexcited carriers are generated in the depletion layer of the photo device, therefore, it is possible to analyze a characteristic of the photo device. In the photo device, particularly, it is possible to enhance a performance of the photo device by increasing an absorption rate of the photoexcited carrier toward an electrode side. For this reason, it is demanded to analyze a process for disappearance of the photoexcited carrier in the photo device.

As one of methods of inspecting the photo device, it is known to utilize a luminous phenomenon. Specifically, when a voltage is applied to the photo device, thereby causing current to flow in a forward direction, an electron and a hole are bonded to each other in a PN junction part so that light (electroluminescent light) is generated. It is known that a defect of the PN junction part of the photo device is examined by utilizing the phenomenon (for example, International Publication No. WO2006/059615).

Moreover, an optical beam induced current (OBIC) method is known as an inspecting technique utilizing light. Specifically, a semiconductor on which an LSI or the like is formed is irradiated with a laser beam, and a photoexcited carrier thus generated is measured as current (Akihiko Ooi, "Technology of the Microscopic Analysis for Semiconductor Devices", Fuji Jihou, Vol. 76, No. 3 (2003) pp. 197-200). The inspecting technique can also be applied to a photo device in addition to the semiconductor such as the LSI.

In the case of the inspecting method described in the Patent Literature 1, however, the electroluminescent light emitted from the photo device is feeble. For this reason, it is very hard to detect the process for disappearance of the photoexcited carrier in the depletion layer of the photo device.

Moreover, in the case of the inspecting method described in the Non-Patent Literature 1, a connection (wiring) for leading the photoexcited carrier generated in the depletion layer is required for measuring current. For this reason, it is necessary to cause a probe to come in contact with an electrode in the vicinity of the depletion layer in order to measure the photoexcited carrier with high precision. Accordingly, in the case in which the electrode is formed finely, it is hard to cause the probe to come in contact therewith. Moreover, in the case in which the probe is formed of a metal, the probe is caused to come in contact with the semiconductor so that there is a fear that the semiconductor might be damaged minutely or contaminated with a metal ion or the like. For this reason, there is demanded a technique for inspecting the photo device in non-contact as greatly as possible.

SUMMARY OF THE INVENTION

The present invention is directed for a device for inspecting a photo device.

According to the present invention, the inspecting device includes a detection part having a detector for detecting an electric field intensity of an electromagnetic wave pulse depending on irradiation with probe light emitted from a light source for pulsed light, a delay part for changing a time difference between a time that the electromagnetic wave pulse arrives at the detector and a time that the probe light arrives at the detector, thereby delaying a timing for detecting the electromagnetic wave pulse through the detector, a temporal waveform restoration part for restoring a temporal waveform of the electromagnetic wave pulse based on the electric field intensity of the electromagnetic wave pulse detected by the detector in the plurality of pieces of detection timing, and an electromagnetic wave pulse analysis part for detecting a negative peak of the electric field intensity in the temporal waveform.

By the irradiation of the photo device with the pulsed light, photoexcited carriers (a free electron and a free hole) are generated. The photoexcited carriers thus generated are accelerated by an electric field which is present in a depletion layer or the like so that photocurrent is generated. At this time, there is radiated an electromagnetic wave (an electromagnetic wave pulse) which is proportional to a time differential of the photocurrent. The photoexcited carriers thus generated are absorbed into an electrode provided in the photo device or are recombined to disappear. For this reason, the photocurrent dissipates. At this time, the electric field intensity of the electromagnetic wave pulse to be radiated takes the negative peak. By detecting the negative peak of the electric field intensity in the electromagnetic wave pulse which is restored, accordingly, it is possible to detect the disappearance of the photoexcited carriers. Since the electromagnetic wave pulse radiated from the photo device is detected, furthermore, it is possible to carry out the inspection in non-contact as greatly as possible.

It is preferable that the electromagnetic wave pulse analysis part should detect two negative peaks of the electric field intensity in the temporal waveform and should standardize an electric field intensity of a second one of the two negative peaks which is detected later based on an electric field intensity of a first one of them which is detected earlier.

The electric field intensity of the second negative peak generated in the disappearance of the photoexcited carrier is standardized with the electric field intensity of the first negative peak generated in the generation of the photoexcited carrier. When the electric field intensity of the second negative peak is measured in a plurality of positions in the photo device, consequently, it is possible to compare respective results of measurement more accurately.

It is preferable that there should further be provided a moving mechanism for relatively moving the photo device with respect to the irradiation part, and a control part for controlling the delay part, thereby changing the detection timing. The control part controls the delay part in order to measure, in a predetermined measuring timing, an electromagnetic wave pulse to be radiated from each position of the photo device when irradiating the photo device with the pulsed light while moving the photo device relatively by means of the moving mechanism, and the measuring timing is determined based on a timing for detecting the two negative peaks in a temporal waveform of the electromagnetic wave pulse radiated depending on the irradiation with the pulsed light in a plurality of positions of the photo device in advance.

When a wide range in the photo device is to be inspected, it is possible to carry out the inspection in a short time.

It is preferable that the photo device should constitute a solar cell.

A process for the disappearance of the photoexcited carrier in the solar cell can be inspected in non-contact as greatly as possible.

Moreover, the present invention is directed to a method of inspecting a photo device.

According to the present invention, the inspecting method includes the steps of (a) irradiating the photo device with pulsed light, (b) detecting, through a detector, an electric field intensity of an electromagnetic wave pulse to be radiated from the photo device in the step (a) depending on irradiation with probe light emitted from a light source for the pulsed light, (c) changing a time difference between a time that the electromagnetic wave pulse arrives at the detector and a time that the probe light arrives at the detector, thereby delaying a timing for detecting the electromagnetic wave pulse through the detector in the step (b), (d) restoring a temporal waveform of the electromagnetic wave pulse based on the electric field intensity of the electromagnetic wave pulse detected in the plurality of pieces of detection timing in the step (b), and (e) detecting a negative peak of the electric field intensity in the temporal waveform restored in the step (d).

Therefore, it is an object of the present invention to provide a technique for inspecting a process for disappearance of a photoexcited carrier in a depletion layer of a photo device in non-contact as greatly as possible.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a diagram showing a schematic structure of an inspecting device according to a first preferred embodiment;

FIG. 3 is a schematic sectional view showing a solar cell;

FIG. 5 is a plan view showing the solar cell seen from a back side;

FIG. 6 is a flow chart showing an example of an inspection for the solar cell;

FIG. 11 is a chart showing a spectral distribution of an electromagnetic wave pulse;

FIG. 12 is a diagram showing schematic structures of an irradiation part and a detection part in an inspecting device according to a second preferred embodiment; and FIG. 13 is a diagram showing schematic structures of an irradiation part and a detection part in an inspecting device according to a third preferred embodiment.

DESCRIPTION OF THE PREFERRED EMBODIMENTS

Preferred embodiments according to the present invention will be described below with reference to the accompanying drawings. The following preferred embodiments are specifically illustrative as the present invention and do not restrict the technical scope of the present invention. In FIG. 1 and subsequent drawings, for easy understanding, dimensions or numbers of respective parts are exaggerated or simplified and shown as necessary in some cases.

<1. First Preferred Embodiment>

<1. 1 Structure and Function of Inspecting Device>

Figure 2:
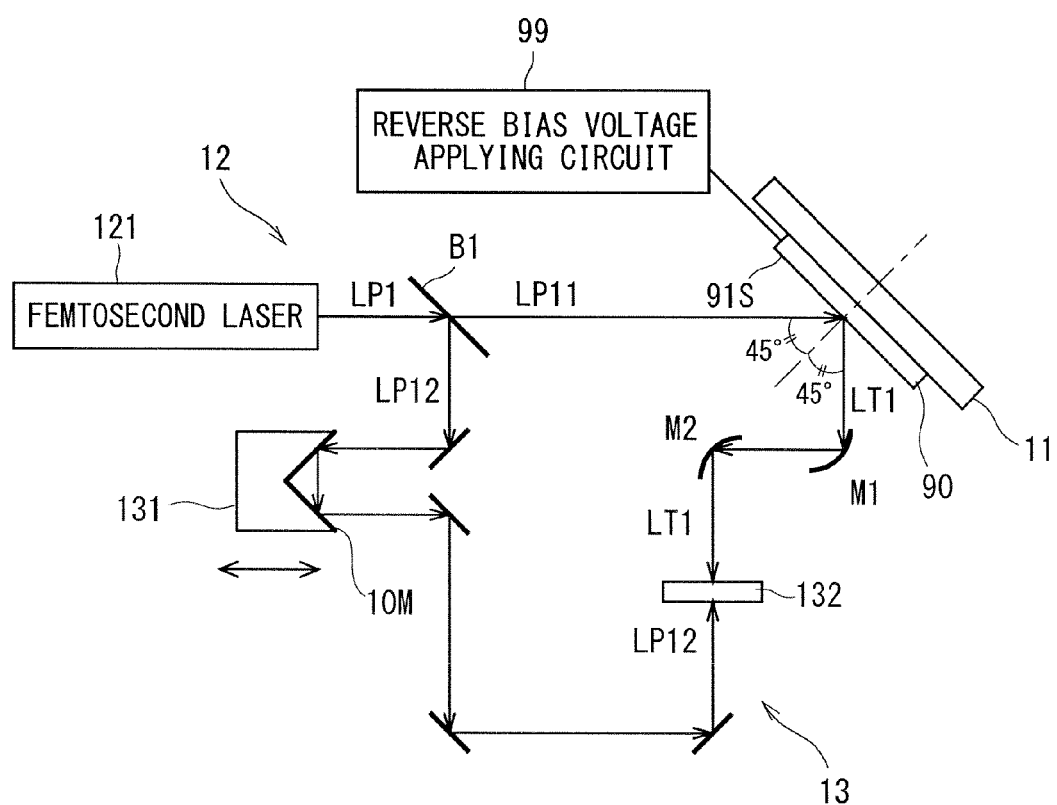
FIG. 2 is a diagram showing schematic structures of an irradiation part and a detection part illustrated in FIG. 1.

FIG. 1 is a diagram showing a schematic structure of an inspecting device 100 according to a first preferred embodiment. Moreover, FIG. 2 is a diagram showing schematic structures of an irradiation part 12 and a detection part 13 illustrated in FIG. 1. The inspecting device 100 has a suitable structure for inspecting a characteristic of a depletion layer of a solar cell 90 to be a kind of a substrate on which a photo device is formed.

The photo device such as a solar cell has a pn junction part in which p-type and n-type semiconductors are bonded to each other, for example. There is generated diffusion current through which an electron and a hole are diffused and bonded to each other in the vicinity of the pn junction part. Consequently, there is formed a depletion layer in which the electron and the hole are rarely present in the vicinity of the pn junction part. In the region, force for bringing the electron and the hole back to n-type and p-type regions respectively is generated. For this reason, an electric field (an internal electric field) is generated in the photo device.

In the case in which the pn junction part is irradiated with light having energy exceeding a band gap, a free electron and a free hole which are generated in the pn junction part are moved to the n-type semiconductor side and the p-type semiconductor side through the internal electric field respectively. In the photo device, the current is taken out through electrodes attached to the n-type semiconductor and the p-type semiconductor respectively. For example, in the case of the solar cell, the movement of the free electron and the free hole generated in the irradiation of the depletion layer of the pn junction part with the light is utilized as DC current.

The inventors found that an electromagnetic wave pulse having a specific wavelength is generated when the photo device is irradiated with pulsed light having a predetermined wavelength. According to Maxwell's equations, when current is changed, there is generated an electromagnetic wave having an intensity which is proportional to a time differential of the current. In other words, a photoexcited carrier generation region such as the depletion layer is irradiated with the pulsed light so that generation and disappearance of photocurrent occur instantaneously. It is supposed that an electromagnetic wave pulse is generated in proportion to a time differential of the photocurrent generated instantaneously.

The generation of the photocurrent reflects a characteristic of the photoexcited carrier generation region such as the depletion layer. By analyzing the generated electromagnetic wave pulse, accordingly, it is possible to inspect the characteristic of the photoexcited carrier generation region such as the depletion layer. Based on the principle, the inspecting device 100 is constituted to detect the electromagnetic wave pulse generated when the solar cell 90 is irradiated with pulsed light having a predetermined wavelength.

As shown in FIG. 1, the inspecting device 100 includes a stage 11, the irradiation part 12, the detection part 13, a visible camera 14, a motor 15, a control part 16, a monitor 17 and an operation input part 18.

The solar battery 90 is fixed onto the stage 11 by fixing means which is not shown. As the fixing means, there is assumed means utilizing an interposing tool for interposing a substrate, an adhesive sheet, an adsorption hole formed on a surface of the stage 11, or the like. If the solar cell 90 can be fixed, however, it is also possible to employ the other fixing means. In the present preferred embodiment, the stage 11 holds the solar cell 90 in such a manner that the irradiation part 12 and the detection part 13 are disposed on a light receiving surface side 91S side of the solar cell 90.

As shown in FIG. 2, the irradiation part 12 includes a femtosecond laser 121. The femtosecond laser 121 radiates pulsed light (pulsed light LP1) having a wavelength including a visible light region of 360 nm (nanometers) to 1 μm (micrometer), for example. As a specific example, pulsed light to be linearly polarized light having a center wavelength in the vicinity of 800 nm, a cycle of several kHz to several hundreds MHz, and a pulse width of approximately 10 to 150 femtoseconds is radiated from the femtosecond laser. As a matter of course, pulsed light in the other wavelength range (having a visible light wavelength such as a blue wavelength (450 to 495 nm) or a green wavelength (495 to 570 nm)) may be emitted.

The pulsed light LP1 emitted from the femtosecond laser 121 is divided into two portions by means of a beam splitter B1. The solar cell 90 is irradiated with pulsed light (pulsed light LP11) obtained by the division. At this time, the irradiation part 12 irradiates with the pulsed light LP11 from the light receiving surface 91S side. Moreover, the solar cell 90 is irradiated with the pulsed light LP11 in such a manner that an optical axis of the pulsed light LP11 is obliquely incident on the light receiving surface 91S of the solar cell 90. In the present preferred embodiment, an irradiation angle is set in such a manner that an incidence angle is 45 degrees. However, the incidence angle is not restricted to the angle but can be properly changed in a range of zero to 90 degrees.

Figure 4:
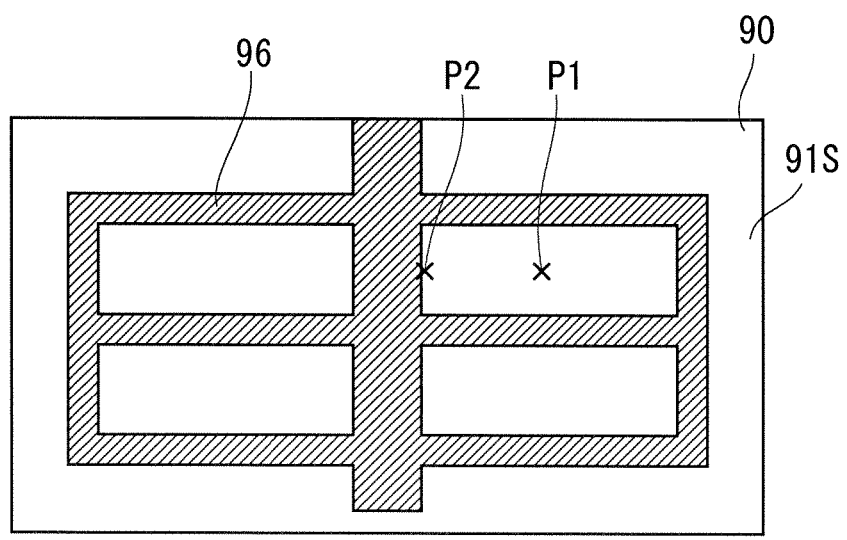
FIG. 4 is a plan view showing the solar cell seen from a light receiving surface side.

FIG. 3 is a schematic sectional view showing the solar cell 90. Moreover, FIG. 4 is a plan view showing the solar cell 90 seen from the light receiving surface 91S side. Furthermore, FIG. 5 is a plan view showing the solar cell 90 seen from a back side. The solar cell 90 is constituted as a solar panel which is crystal silicon based. The solar cell 90 is constituted as a crystal silicon based solar cell having a laminated structure including a flat back electrode 92 formed of aluminum or the like, a p-type silicon layer 93, an n-type silicon layer 94, an antireflection film 95, and a grid-like light receiving surface electrode 96 in order from a bottom. The antireflection film 95 is formed of silicon oxide, silicon nitride, titanium oxide or the like.

Any of main surfaces of the solar cell 90 at a side where the light receiving surface electrode 96 is provided serves as the light receiving surface 91S. In other words, the solar cell 90 is designed to receive light from the light receiving surface 91S side, thereby generating power. A transparent electrode may be used for the light receiving surface electrode 96. The inspecting device 100 may be applied to an inspection for a solar cell (an amorphous silicon based solar cell or the like) other than a crystal silicon based solar cell. In the case of the amorphous silicon based solar cell, generally, an energy gap is 1.75 eV to 1.8 eV which is larger than an energy gap of the crystal silicon based solar cell, that is, 1.2 eV. In this case, it is possible to generate a terahertz wave well in the amorphous silicon based solar cell by setting the wavelength of the femtosecond laser 121 to be 700 μm or less, for example. Based on the same thinking way, the inspecting device 100 can also be applied to other semiconductor solar cells (CIGS and GaAS based solar cells and the like).

In order to suppress a reflection loss of light, the light receiving surface 91S of the solar cell 90 has a predetermined texture structure. Specifically, concavo-convex portions having a size of several μm to several tens μm are formed by anisotropic etching or the like or a V-shaped groove is formed by a mechanical method. Thus, the light receiving surface 91S of the solar cell 90 is generally formed to enable lighting as efficiently as possible. When the light receiving surface 91S is irradiated with pulsed light having a predetermined wavelength, accordingly, the pulsed light easily reaches the pn junction part 97. For example, in the case of the solar panel, light having a wavelength of 1 μm or less and mainly including a wavelength range of a visible light can easily reach the pn junction part 97 if any.

Moreover, a bonding portion of the p-type silicon layer 93 and the n-type silicon layer 94 serves as a pn junction part 97 in which a depletion layer is formed. When this part is irradiated with the pulsed light LP11, an electromagnetic wave pulse is generated and emitted to an outside. In the present preferred embodiment, an electromagnetic wave pulse to be detected by the detection part 13 is an electromagnetic wave pulse having a frequency of 0.01 THz to 10 THz (which will be hereinafter referred to as an electromagnetic wave pulse LT1).

Returning to FIG. 2, the other pulsed light obtained by the division of the beam splitter B1 is incident, as probe light LP12, on a detector 132 via a delay part 131, a mirror and the like. Moreover, the electromagnetic wave pulse LT1 generated depending on the irradiation with the pulsed light LP11 is collected in parabolic mirrors M1 and M2 and is then incident on the detector 132.

The detector 132 includes a photoconductive switch as an electromagnetic wave detection element, for example. When the detector 132 is irradiated with the probe light LP12 in a state in which the electromagnetic wave pulse is incident on the detector 132, current corresponding to an electric field intensity of the electromagnetic wave pulse LT1 is instantaneously generated in the photoconductive switch. The current corresponding to the electric field intensity is converted into a digital quantity through an I/V conversion circuit, an A/D conversion circuit or the like. Thus, the detection part 13 detects an electric field intensity of the electromagnetic wave pulse LT1 transmitted through the solar cell 90 depending on the irradiation with the probe light LP12. It can also be supposed that another element, for example, a nonlinear optical crystal is applied to the detector 132.

The delay part 131 is an optical element for continuously changing an arrival time of the probe light LP12 from the beam splitter B1 to the detector 132. The delay part 131 is fixed to a moving stage (not shown) to move in a direction of incidence of the probe light LP12. Moreover, the delay part 131 includes a return mirror 10M for returning the probe light LP12 in the direction of incidence.

The delay part 131 drives the moving stage based on control of the control part 16 to move the return mirror 10M, thereby changing an optical path length of the probe light LP12 precisely. Consequently, the delay part 131 changes a time difference between a time that the electromagnetic wave pulse LT1 arrives at the detection part 13 and a time that the probe light LP12 arrives at the detection part 13. By changing the optical path length of the probe light LP12 through the delay part 131, accordingly, it is possible to delay a timing (a detection timing or a sampling timing) for detecting the electric field intensity of the electromagnetic wave pulse LT1 in the detection part 13 (the detector 132).

It is also supposed to change the time that the probe light LP12 arrives at the detection part 13 in another mode. Specifically, it is preferable to utilize an electro-optical effect. In other words, it is also possible to use, as a delay element, an electro-optic element having a refractive index changed through a variation in a voltage to be applied. Specifically, it is possible to utilize the electro-optic element disclosed in Japanese Patent Application Laid-Open No. 2009-175127.

Furthermore, it is also possible to change an optical path length of the pulsed light LP11 (a pump beam) or an optical path length of the electromagnetic wave pulse LT1 radiated from the solar cell 90. Also in this case, a time that the electromagnetic wave pulse LT1 arrives at the detector 132 can be relatively shifted from a time that the probe light LP12 arrives at the detector 132. Consequently, it is possible to delay the timing for detecting the electric field intensity of the electromagnetic wave pulse LT1 in the detector 132.

In addition, a reverse bias voltage applying circuit 99 is connected to the solar cell 90. The reverse bias voltage applying circuit 99 serves to apply a reverse bias voltage between the back electrode 92 and the light receiving surface electrode 96 in the inspection. The reverse bias voltage is applied between voltages so that the depletion layer of the pn junction part 97 can be increased. Consequently, it is possible to increase the electric field intensity of the electromagnetic wave pulse LT1 to be detected in the detector 132. Therefore, it is possible to enhance detection sensitivity of the electromagnetic wave pulse LT1 in the detection part 13. However, it is also possible to omit the reverse bias voltage applying circuit 99.

Returning to FIG. 1, the visible camera 14 is constituted by a CCD camera and includes an LED or a laser as a photographing light source. The visible camera 14 is used for photographing the whole solar cell 90 or photographing a position to be irradiated with the pulsed light LP11. Image data acquired by the visible camera 14 are transmitted to the control part 16 and is displayed on the monitor 17 or the like.

The motor 15 drives an X-Y table (not shown) having the stage 11 in a two-dimensional surface. The motor 15 drives the X-Y table, thereby moving the solar cell 90 held on the stage 11 relatively with respect to the irradiation part 12. The inspecting device 100 can move the solar cell 90 to an optional position in the two-dimensional surface by means of the motor 15. The inspecting device 100 can irradiate a wide range of the solar cell 90 (an inspecting target region) with the pulsed light LP11 by means of the motor 15, thereby carrying out an inspection.

It is also possible to provide moving means for moving the irradiation part 12 and the detection part 13 in the two-dimensional surface in place of the movement of the solar cell 90 or together with the movement of the solar cell 90. Also in these cases, it is possible to detect the electromagnetic wave pulse LT1 for each region of the solar cell 90. Moreover, the motor 15 may be omitted and the stage 11 may be moved manually by an operator.

The control part 16 has a structure of a general computer including a CPU, an ROM, an RAM, an auxiliary storage part (for example, a hard disk) and the like which are not shown. The control part 16 is connected to the femtosecond laser 121 of the irradiation part 12, the delay part 131 and the detector 132 in the detection part 13, and the motor 15, and controls these operations and receives data therefrom.

More specifically, the control part 16 receives data on the electric field intensity of the electromagnetic wave pulse LT1 from the detector 132. Furthermore, the control part 16 controls the movement of the moving stage (not shown) for moving the delay part 131, and receives, from the delay part 131, data on a position of the delay part 131, for example, a travel distance of the return mirror 10M through a linear scale provided in the moving stage or the like.

Moreover, the control part 16 includes a temporal waveform restoration part 21, an electromagnetic wave pulse analysis part 23 and an image generation part 25, and causes these processing parts to execute a large variety of calculation processing. These processing parts are functions to be implemented through an operation of the CPU in accordance with a program. A part or all of the functions of the processing parts may be implemented by the CPU provided in another computer or may be implemented on a hardware basis by means of a dedicated arithmetic circuit.

Referring to the electromagnetic wave pulse LT1 generated in the solar cell 90, the temporal waveform restoration part 21 establishes a temporal waveform of the electromagnetic wave pulse LT1 based on the electric field intensity detected by the detection part 13 (the detector 132). Specifically, the return mirror 10M of the delay part 131 is moved to change the optical path length of the probe light LP12 (an optical path length of a first optical path), thereby varying a time that the probe light arrives at the detector 132. Consequently, there is changed the timing for detecting the electric field intensity of the electromagnetic wave pulse LT1 in the detector 132. Thus, the temporal waveform restoration part 21 detects the electric field intensity of the electromagnetic wave pulse LT1 in a different phase and plots the same onto a time base, thereby restoring the temporal waveform of the electromagnetic wave pulse LT1.

The electromagnetic wave pulse analysis part 23 analyzes the temporal waveform restored by the temporal waveform restoration part 21. The electromagnetic wave pulse analysis part 23 detects a peak of the electric field intensity in the temporal waveform of the electromagnetic wave pulse LT1 restored by the temporal waveform restoration part 21 and thus detects a change in the intensity of the electromagnetic wave pulse LT1 which is radiated, thereby analyzing a characteristic of the solar cell 90. The details will be described below.

Referring to the inspecting target region of the solar cell 90 (a part or whole of the solar cell 90), the image generation part 25 generates an image obtained by visualizing the distribution of the electric field intensity of the electromagnetic wave pulse LT1 radiated in the irradiation with the pulsed light LP11. Specifically, the image generation part 25 generates an electric field intensity distribution image having a difference in the electric field intensity expressed by a color, a pattern or the like for each measuring position.

The monitor 17 and the operation input part 18 are connected to the control part 16. The monitor 17 is a display device such as a liquid crystal display and serves to display various image information for an operator. The monitor 17 displays an image of the light receiving surface 91S of the solar cell 90 which is photographed by the visible camera 14, a temporal waveform of the electromagnetic wave pulse LT1 which is restored by the temporal waveform restoration part 21, an analysis result obtained by the electromagnetic wave pulse analysis part 23, an electric field intensity distribution image generated by the image generation part 25 or the like. In addition, the monitor 17 displays a necessary GUI (Graphical User Interface) screen for setting a condition of an inspection or the like.

The operation input part 18 is constituted by various input devices, for example, a mouse, a keyboard and the like. The operator can carry out a predetermined operation input through the operation input part 18. The monitor 17 may be constituted as a touch panel to function as the operation input part 18.

The structure of the inspecting device 100 has been described above. Next, specific description will be given to an inspection for the solar cell 90 which is to be carried out by using the inspecting device 100.

<1. 2. Inspection for Solar Cell>

FIG. 6 is a flow chart showing an example of the inspection for the solar cell 90. In the following description, it is assumed that each operation of the inspecting device 100 is controlled by the control part 16 unless otherwise mentioned. Moreover, depending on the contents of a process, a plurality of steps may be executed in parallel or order for executing the steps may be changed appropriately.

First of all, the solar cell 90 to be the inspecting target is fixed to the stage 11 (FIG. 6: Step S11). In Step S11, the solar cell 90 may be delivered into the stage 11 by the operator or the solar cell 90 may be delivered into the stage 11 by a delivery device which is not shown, or the like. At this time, the solar cell 90 is provided in such a manner that the light receiving surface 91S of the solar cell 90 is irradiated with the pulsed light LP11 as described above.

When the solar cell 90 is provided on the stage 11, the reverse bias voltage applying circuit 99 is connected to respective terminals (the back electrode 92 and the light receiving surface electrode 96) of the solar cell 90 so that a reverse bias voltage is applied (FIG. 6: Step S12). Step S12 can also be omitted.

Next, a measuring detection timing through the detection part is set (FIG. 6: Step S13). Specifically, the position of the return mirror 10M is adjusted and secured in such a manner that the control part 16 controls the delay part 131 and the timing for the probe light LP12 to arrive at the detector 132 is thus fixed to a predetermined detection timing. In the present preferred embodiment, the measuring detection timing is set corresponding to a second negative peak in the temporal waveform of the electromagnetic wave pulse LT1 as will be described below. A method of setting the measuring detection timing will be described with reference to FIGS. 7 to 9.

Figure 7:
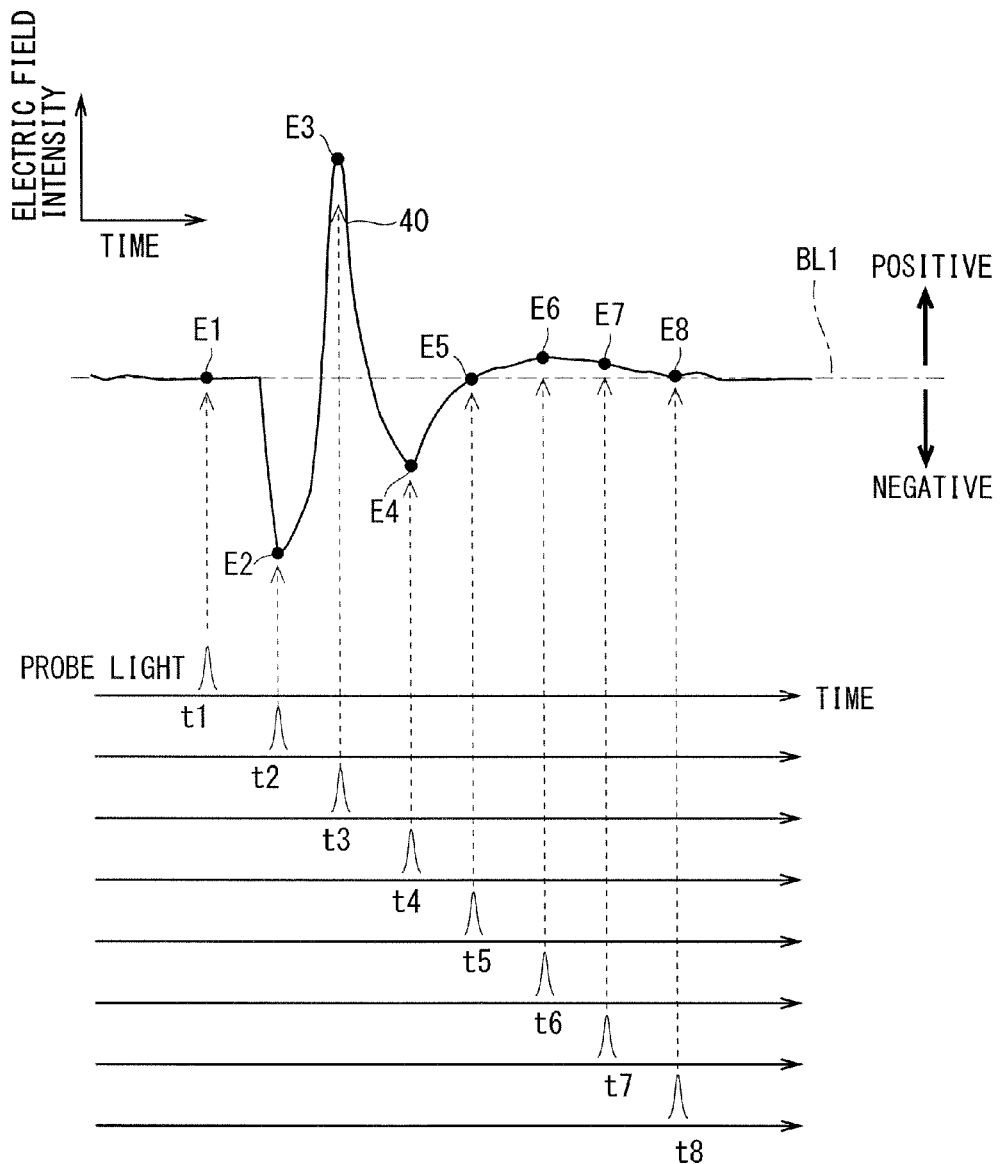
FIG. 7 is a chart showing an example of a temporal waveform of an electromagnetic wave pulse constructed by a temporal waveform restoration part.

FIG. 7 is a chart showing an example of a temporal waveform 40 of the electromagnetic wave pulse LT1 which is built by the temporal waveform restoration part 21. An axis of abscissa in a graph shown in FIG. 7 indicates a time. An axis of ordinate indicates an electric field intensity. Moreover, at a lower side of the graph in FIG. 7, there are conceptually shown the probe lights LP12 in which pieces of timing (t1 to t8) for arriving at the detector 132 are different from each other through the delay part 131.

When a position of the solar cell 90 where the depletion layer is formed is irradiated with the pulsed light LP11, the electromagnetic wave pulse LT1 indicative of the temporal waveform 40 shown in FIG. 7 repetitively arrives at the detector 132 in a cycle which is coincident with a pulse cycle of the pulsed light LP11. A base line BL1 shown in FIG. 7 indicates an electric field intensity (hereinafter referred to as a "reference electric field intensity") in a normal state in which the electromagnetic wave pulse LT1 is not generated. Moreover, a higher electric field intensity than the reference electric field intensity is set to be a positive electric field intensity and a lower electric field intensity than the reference electric field intensity is set to be a negative electric field intensity.

For example, in the case in which the delay part 131 is regulated in such a manner that the probe light LP12 arrives at the detector 132 in the detection timing t1, an electric field intensity having a value E1 is detected by the detector 132. Moreover, when the delay part 131 is regulated so that the pieces of detection timing are delayed into t2 to t8 respectively, electric field intensities having values E2 to E8 are detected by the detection part 13.

Thus, in the case in which the temporal waveform of the electromagnetic wave pulse LT1 radiated from the solar cell 90 is restored, the delay part 131 is controlled so that the detection timing is changed finely and the electric field intensity of the electromagnetic wave pulse LT1 in each detection timing is measured. The temporal waveform restoration part 21 plots an electric field intensity value thus acquired onto the graph along the time base so that the temporal waveform 40 of the electromagnetic wave pulse LT1 is restored.

Figure 8:
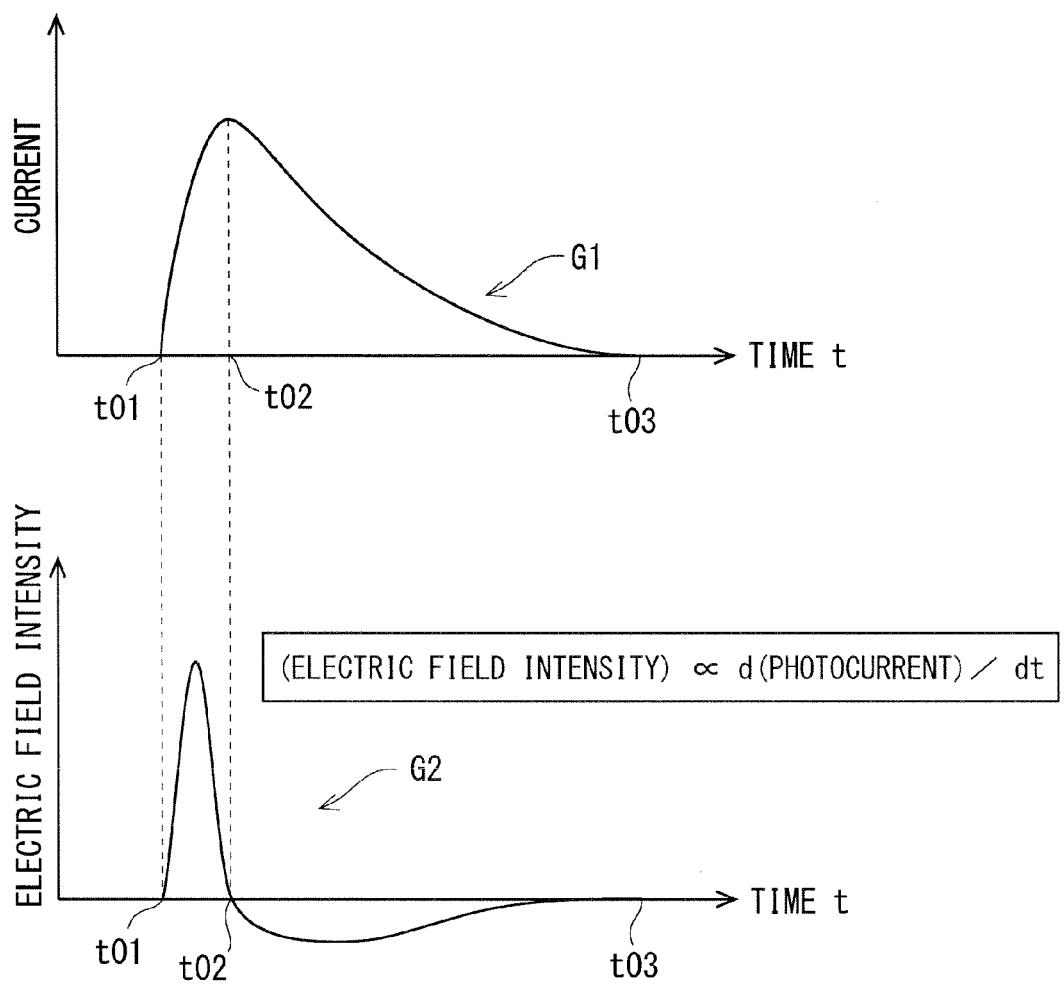
FIG. 8 is a chart conceptually showing photocurrent to be generated by irradiating with pulsed light and an electromagnetic wave pulse to be radiated depending on the photocurrent.

FIG. 8 is a chart conceptually showing photocurrent G1 to be generated by the irradiation with the pulsed light LP11 and an electromagnetic wave pulse G2 to be radiated depending on the photocurrent. In a graph shown in FIG. 8, an axis of abscissa indicates a time. Moreover, an axis of ordinate indicates current in the graph of the photocurrent G1 and indicates an electric field intensity in the graph of the electromagnetic wave pulse G2.

As described above, a photoexcited carrier is generated in the vicinity of the depletion layer of the pn junction part 97 in the solar cell 90 by the irradiation with the pulsed light LP11. The photoexcited carrier is accelerated by an internal electric field generated through a Schottky barrier junction or the like to the depletion layer or the metal (the back electrode 92, the light receiving surface electrode 96 or the like) or an external electric field generated by applying a reverse bias voltage. As shown in FIG. 8, consequently, the photocurrent G1 is increased between times t01 to t02. The generated photoexcited carrier disappears due to absorption into an electrode or recombination of an electron and a hole. For this reason, as shown in FIG. 8, the photocurrent G1 is decreased between times t02 to t03.

According to the Maxwell's equations, an electromagnetic wave is generated in proportion to a time differential of photocurrent. For this reason, the electromagnetic wave pulse G2 theoretically indicates a positive electric field intensity depending on increase in the photocurrent G1 between the times t01 to t02 and indicates a negative electric field intensity depending on decrease in the photocurrent G1 between the times t02 to t03 as shown in FIG. 8.

In order to enhance power generation efficiency of the solar cell, it is demanded to efficiently move the photoexcited carrier separated by the depletion layer of the pn junction part 97 to an electrode without recombination. In other words, it is important to analyze a dynamic behavior (particularly, a process for disappearance) of the photoexcited carrier. In the present preferred embodiment, therefore, the electric field intensity of the electromagnetic wave pulse G2 in the decrease in the photocurrent G1 is varied so that the process for the disappearance of the photoexcited carrier is detected.

When the solar cell 90 is irradiated with the pulsed light LP11, the electric field intensity of the typical electromagnetic wave pulse LT1 radiated from the solar cell 90 first fluctuates toward a negative side in the normal state to take a negative peak (a first negative peak, the detection timing t2) and to then take a second negative peak (a second negative peak, the detection timing t4) via a positive peak (the detection timing t3) as shown in FIG. 7.

Referring to a factor of the generation of the first negative peak, a correct theory has not been established academically and there are a large number of unclear points. On the other hands, the positive peak is generated depending on the increase in the photocurrent G1 as described with reference to FIG. 8. Moreover, it is supposed that the second negative peak is generated depending on the decrease in the photocurrent G1.

As described with reference to FIG. 8, the electric field intensity of the electromagnetic wave is a differential component of the photocurrent. For this reason, it can be guessed that an absorption rate of the photoexcited carrier through the electrode is high or a recombination degree is high in the case in which the second negative peak of the electromagnetic wave pulse LT1 is high (a great absolute value). On the other hand, it can be guessed that the absorption rate of the photoexcited carrier through the electrode is low or the recombination degree is low in the case in which the absolute value of the second negative peak is small.

By measuring the absolute value of the second negative peak, thus, it is possible to analyze the disappearance of the photoexcited carrier. In the inspection for the solar cell 90 according to the present preferred embodiment, therefore, the measuring detection timing is set in such a manner that the detector 132 takes a timing for detecting the second negative peak of the electromagnetic wave pulse LT1 (t4 in the example shown in FIG. 7) in Step S13 illustrated in FIG. 6.

The measuring detection timing is determined by restoring the temporal waveform of the electromagnetic wave pulse LT1 radiated through previous experimental irradiation with the pulsed light LP11 on the solar cell 90. However, there is a possibility that the timing for the electric field intensity of the electromagnetic wave pulse LT1 to take the second negative peak might be varied every measuring position of the solar cell 90. For this reason, the electromagnetic wave pulse LT1 radiated in some measuring positions is restored in advance and the timing for taking the second negative peak is acquired in each temporal waveform thus restored. The measuring detection timing in Step S13 may be determined corresponding to a timing obtained by averaging the plurality of pieces of timing thus acquired. This respect will be described specifically with reference to FIG. 9.

Figure 9:
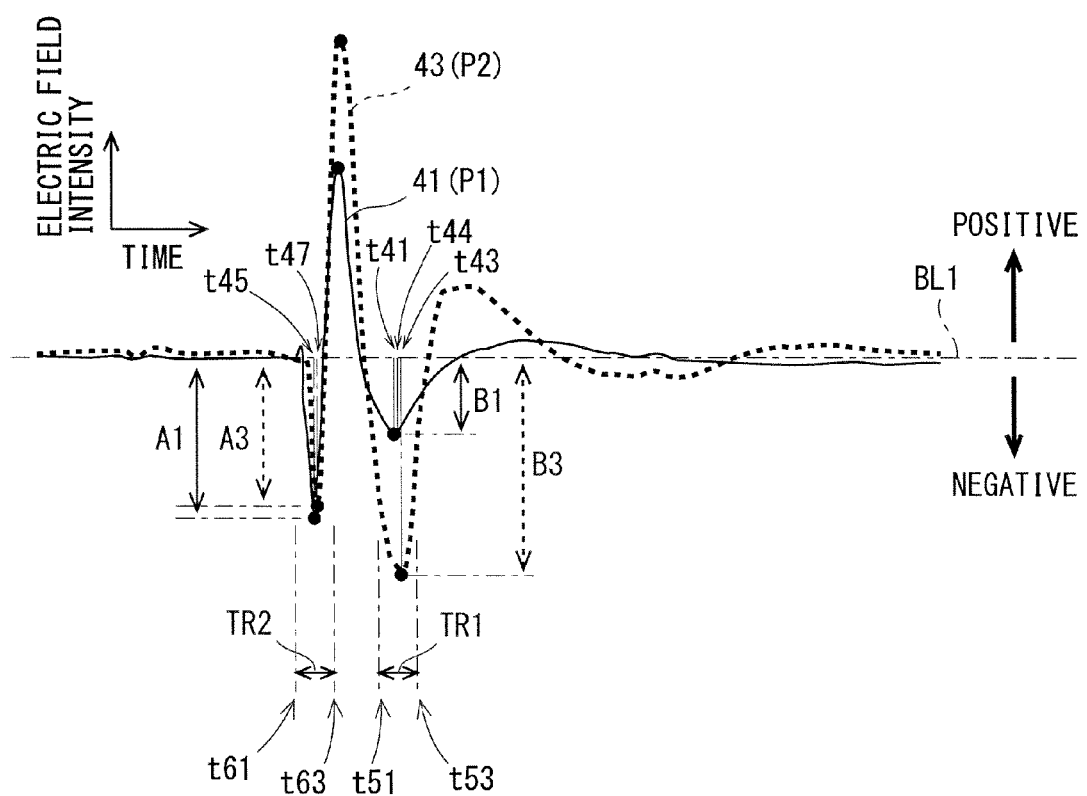
FIG. 9 is a chart showing temporal waveforms of electromagnetic wave pulses radiated in a plurality of measuring positions.

FIG. 9 is a chart showing temporal waveforms 41 and 43 of the electromagnetic wave pulse LT1 radiated in measuring positions P1 and P2. In FIG. 9, the temporal waveform 41 shown in a solid line corresponds to the electromagnetic wave pulse LT1 to be radiated when the measuring position P1 of the solar cell 90 illustrated in FIG. 4 is irradiated with the pulsed light LP11. Moreover, the temporal waveform 43 shown in a broken line corresponds to the electromagnetic wave pulse LT1 to be radiated when the measuring position P2 of the solar cell 90 illustrated in FIG. 4 is irradiated with the pulsed light LP11. As shown in FIG. 4, the measuring position P1 is closer to the electrode (the light receiving surface electrode 96) than the measuring position P2.

As shown in FIG. 9, pieces of timing for the electric field intensity to take the second negative peak are represented by t41 and t43 in the temporal waveforms 41 and 43 respectively, and they are slightly different from each other. Therefore, the measuring detection timing is set corresponding to an average (t44) of the pieces of timing t41 and t43. As a matter of course, it is also impossible to prevent the temporal waveform from being restored and to inhibit the timing obtained by averaging the pieces of timing for taking the respective second negative peaks from being set to the measuring detection timing in more places. As a matter of course, the measuring detection timing may be adapted to either t41 or t43.

When the detection timing is set corresponding to the timing determined as described above, the motor 15 is driven to move the solar cell 90 in the two-dimensional surface (FIG. 6: Step S14). At this time, the solar cell 90 is irradiated with the pulsed light LP11 so that the electric field intensity of the electromagnetic wave pulse LT1 to be radiated is measured. Consequently, an electric field intensity distribution for the inspecting target region of the solar cell 90 is acquired.

As an example of the movement of the solar cell 90 in Step S14, the solar cell 90 is moved in a predetermined first direction (a horizontal scanning direction) to once cause the pulsed light LP11 to carry out a scan from an end to an end in the inspecting target region, for instance. Then, the solar cell 90 is moved (shifted) corresponding to a required distance in a second direction (a vertical scanning direction) which is orthogonal to the first direction to move the solar cell 90 in the first direction again. By repetitively moving the solar cell 90, it is possible to cause the pulsed light LP11 to carry out the scan for the inspecting target region of the solar cell 90.

When the electric field intensity of the electromagnetic wave pulse LT1 is acquired in Step S14, an image indicative of an electric field intensity distribution (an image of imaging) is created by the image generation part 25 and is displayed on the monitor 17 (FIG. 6: Step S15).

Figure 10:
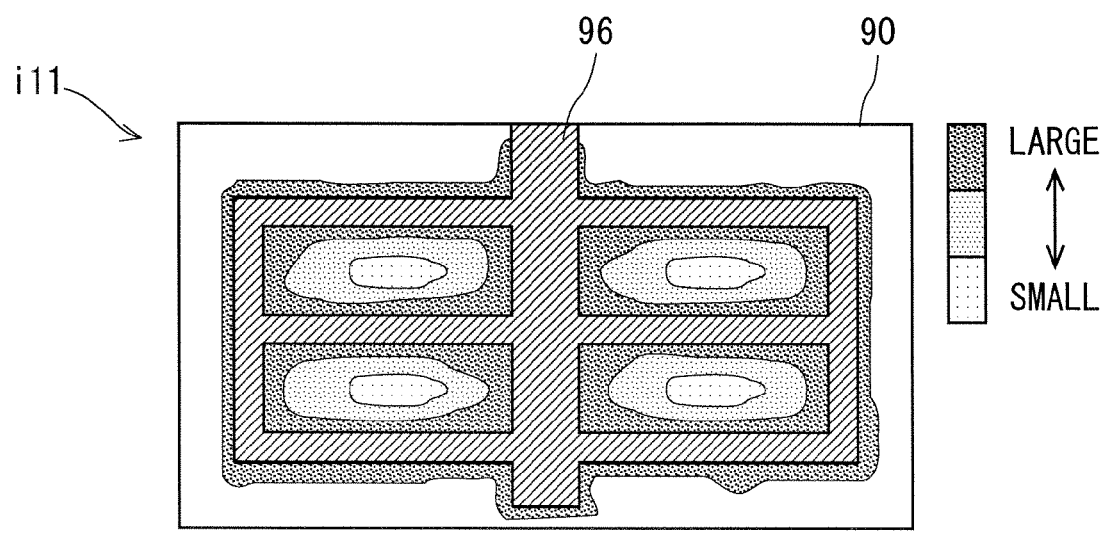
FIG. 10 is a typical view showing an image representing an electromagnetic wave intensity distribution.

FIG. 10 is a typical view showing an image of imaging ill representing the electromagnetic wave intensity distribution. The image of imaging ill is generated through coloring depending on the electric field intensity radiated every position (inspecting position) where an image representing the solar cell 90 is irradiated with the pulsed light LP11. For the image representing the solar cell 90, it is also possible to employ an image obtained by photographing through the visible camera 14, an illustration image imitating the solar cell 90 or the like. Although the electric field intensity is expressed in three stages for convenience of description in the typical view shown in FIG. 10, it may be expressed in more stages.

As shown in FIG. 10, generally, the absorption degree of a photoexcited carrier is increased if the measuring position is closer to the electrode (the light receiving surface electrode 96). For this reason, the second negative peak of the electric field intensity is increased in a close portion to the electrode as shown in the image of imaging ill. By acquiring the image of imaging ill, it is possible to grasp the second negative peak at a time every measuring position. Therefore, it is possible to carry out analysis related to the disappearance of the photoexcited carrier within a wide range. According to the image of imaging ill, moreover, it is anticipated that a problem such as a defect of a depletion layer or a contact failure of an electrode is caused in a certain specific position if the electric field intensity (absolute value) in the specific position is smaller than expected, for example. By analyzing the image of imaging ill, therefore, it is possible to easily find out a defective portion in the solar cell 90.

According to the inspecting device 100, moreover, an electromagnetic wave radiated from the solar cell 90 is detected. Therefore, it is possible to carry out the inspection in non-contact as greatly as possible. Consequently, it is not necessary to cause a current or voltage measuring probe pin to come in contact with an electrode as in the conventional inspection. Thus, it is possible to prevent a foreign substance such as a metal ion from sticking to the solar cell 90 or the solar cell 90 from being damaged.

<Other Inspection Mode 1 (Inspection Based on Standardization>

In the inspection shown in FIG. 6, there is measured only the absolute value of the second negative peak in each electromagnetic wave pulse LT1 which is radiated. However, the absolute value of the second negative peak of the electric field intensity is completely a relative value. For this reason, there is a fear that a correct comparison might not be made in the case in which results of measurement in measuring positions are exactly used. Therefore, these results of measurement may be standardized to carry out the inspection. The standardization will be described with reference to FIG. 9.

For example, it is supposed that absolute values (B1, B3) of the second negative peak in the temporal waveforms 41 and 43 shown in FIG. 9 are standardized based on the electric field intensity detected in the other timing in the respective temporal waveforms 41 and 43 respectively if any. For example, it is supposed that absolute values (A1, A3) of the first negative peak are acquired as a standardizing electric field intensity and a value X (=A1/B1 or A3/B3) standardized through a division of the absolute values by the absolute values (B1, B3) of the second negative peak is acquired.

When the value X is smaller than one (that is, A1<B1 or A1<B3), for example, it is possible to evaluate the result of measurement in which the absorption rate of the photoexcited carrier into the electrode is relatively high or the recombination degree is relatively high. Moreover, when the value X is greater than one (that is, A1>B1 or A3>B3), it is possible to evaluate the result of measurement in which the absorption rate of the photoexcited carrier into the electrode is relatively low or the recombination degree is relatively low.

As a matter of course, it is also supposed that the standardizing electric field intensity is set to be an electric field intensity to be detected in a timing other than the first negative peak (for example, an electric field intensity in a positive peak). However, as shown in FIG. 9, a fluctuation in the absolute value (for example, A1, A3) of the first negative peak is relatively smaller than a fluctuation in the absolute value of the other peak (for example, the positive peak, the second negative peak or the like) in the electromagnetic wave pulse LT1 radiated every photoexcited carrier generation region. In the temporal waveforms of the electromagnetic wave pulse LT1 in different measuring positions, an electric field intensity in a timing having a small fluctuation is employed as a standardizing electric field intensity. Consequently, the results of measurement in the measuring positions can be relatively evaluated more accurately.

In the case in which the electric field intensity is standardized, it is necessary to acquire the standardizing electric field intensity and the electric field intensity of the second negative peak every measuring position in the inspecting target region. For this reason, it is preferable that the control part 16 should control the delay part 131 every measuring position, thereby changing the measuring detection timing of the electromagnetic wave pulse LT1 through the detector 132 between a timing for detecting the standardizing electric field intensity and a timing for detecting the electric field intensity of the second negative peak. As a matter of course, it is also possible to once measure either the standardizing electric field intensity or the electric field intensity of the second negative peak and to then measure the other for all of the inspecting target regions.

Moreover, the timing for the electric field intensity to take the first negative peak is varied every measuring position in some cases. For example, the electric field intensity takes the first negative peak in the pieces of timing of t43 and t45 in the temporal waveforms 41 and 43 shown in FIG. 9, respectively. Therefore, it is supposed that the temporal waveform of the electromagnetic wave pulse LT1 to be radiated is previously restored for some measuring positions and an average value of the timing taking the first negative peak in each temporal waveform thus restored is set into the measuring detection timing for detecting the standardizing electric field intensity. In Step S14 shown in FIG. 6, it is preferable that the detector 132 should detect the electromagnetic wave pulse LT1 to be radiated in the determined measuring detection timing when the pulsed light LP11 is caused to carry out a scan. As a matter of course, it is also supposed that the measuring detection timing for detecting the standardizing electric field intensity is determined based on only the temporal waveform of the electromagnetic wave pulse LT1 radiated in a specific position.

<Other Inspection Mode 2>

As described with reference to FIG. 9, the timing for the electric field intensity of the electromagnetic wave pulse LT1 to be radiated to take the second negative peak is varied every measuring position in some cases. In the case in which a shift of the timing is great, it is hard to accurately compare the results of measurement in different measuring positions with each other. Therefore, it is also supposed to accurately measure the absolute value of the second negative peak in the electromagnetic wave pulse LT1 every measuring position.

In this case, the pieces of timing for previously restoring the temporal waveforms of the electromagnetic wave pulse LT1 radiated in some measuring positions and detecting the second negative peak in these temporal waveforms are specified respectively. Then, a measuring period including the pieces of timing is determined. For example, in the case in which the temporal waveforms 41 and 43 shown in FIG. 9 are restored, a measuring period TR1 (t51 to t53) including t41 and t43 is determined. In Step S14 shown in FIG. 6, the delay part 131 is controlled in such a manner that the measuring detection timing of the detector 132 is changed for the measuring period TR1, that is, between t51 and t53 when the pulsed light LP11 is caused to carry out a scan.

In this case, the timing for detecting the electromagnetic wave pulse LT1 is changed between t51 and t53 every measuring position in the inspecting target region in the execution of Step S14. Therefore, it is possible to accurately measure the second negative peak of the electromagnetic wave pulse LT1 to be radiated from each measuring position.

It is supposed that the standardizing electric field intensity described in the <Other Inspection Mode 1> is also acquired in the same procedure as mentioned above. For example, in the case in which the temporal waveforms 41 and 43 shown in FIG. 9 are restored in advance, the pieces of timing for the electric field intensity to take the first negative peak (t45, t47) are specified and a measuring period TR2 (t61 to t63) including these pieces of timing is determined. In Step S14 shown in FIG. 6, the delay part 131 is controlled in such a manner that the measuring detection timing of the detector 132 is changed for the measuring period TR2, that is, between t61 and t63 when the pulsed light LP11 is caused to carry out a scan.

Consequently, an electric field intensity for the measuring period TR2 is acquired every measuring position. Accordingly, it is possible to accurately determine the absolute value of the first negative peak in the electric field intensity every measuring position.

In this case, the detection timing of the standardizing electric field intensity is varied between t61 and t63 every measuring position in the inspecting target region in the execution of Step S14. Therefore, it is possible to accurately measure the first negative peak of the electromagnetic wave pulse LT1 to be radiated from each measuring position.

<Other Inspection Mode 3 (Inspection Based on Spectral Analysis)>

Moreover, in the inspecting device 100, it is also supposed that spectral analysis is carried out based on the electric field intensity of the electromagnetic wave pulse LT1 radiated from the solar cell 90.

FIG. 11 is a chart showing spectral distributions 51 and 53 of the electromagnetic wave pulse LT1. In FIG. 11, an axis of abscissa indicates a frequency and an axis of ordinate indicates a spectral intensity. The spectral distributions 51 and 53 are frequency distributions acquired through Fourier transform of the temporal waveforms 41 and 43 shown in FIG. 9. By acquiring the spectral distribution 51, it is possible to inspect the characteristic of the depletion layer of the pn junction part 97 in detail. For example, in the case in which a spectral intensity of a specific frequency is significantly lower than an assumed reference value (not shown) in the spectral distributions 51 and 53, it is possible to detect a failure of the solar cell 90, that is, a situation in which an impurity for absorbing the specific frequency is contained in the pn junction part or the like. Moreover, it is also supposed to estimate a type or a concentration of the impurity or the like from the absorbed frequency.

In the case in which an inspection based on the spectral distribution is applied to all of the inspecting target regions, there is a fear that a time required for the inspection is increased greatly. Therefore, it is also supposed that an inspection based on the spectral distribution is carried out for only a measuring position decided to be defective through an inspection based on the absolute value of the second negative peak in the electric field intensity.

<2. Second Preferred Embodiment>

Although the optical axis of the pulsed light LP11 is set to be incident obliquely (an incidence angle of 45 degrees) with respect to the light receiving surface 91S of the solar cell 90 in the inspecting device 100 shown in FIG. 1, the incidence angle of the pulsed light LP11 is not restricted thereto.

FIG. 12 is a diagram showing schematic structures of an irradiation part 12A and a detection part 13A in an inspecting device 100A according to a second preferred embodiment. In the following description, elements having the same functions as the components of the inspecting device 100 according to the first preferred embodiment have the same reference numerals and explanation thereof will be omitted.

Also in the inspecting device 100A, pulsed light LP1 emitted from a femtosecond laser 121 is divided into pulsed light LP11 and probe light LP12 through a beam splitter B1. In the inspecting device 100A, however, the pulsed light LP11 obtained by the division is transmitted through a transparent conductive substrate (ITO) 19 and is vertically incident on a light receiving surface 91S of a solar cell 90. Then, any of electromagnetic wave pulses LT1 radiated from the solar cell 90 toward the light receiving surface 91S side depending on the irradiation with the pulsed light LP11 is reflected by the transparent conductive substrate 19 and is collected by a lens, and is thus incident on a detector 132.

Also in the inspecting device 100A including the irradiation part 12A and the detection part 13A, it is possible to detect the electromagnetic wave pulse LT1 radiated from the solar cell 90 depending on the irradiation with the pulsed light LP11. Therefore, in the same manner as the inspecting device 100 according to the first preferred embodiment, the inspecting device 100A can inspect a characteristic of a photoexcited carrier generation region such as a depletion layer of the solar cell 90 in non-contact as greatly as possible. By the inspecting device 100A, similarly, it is possible to inspect a process for disappearance of the photoexcited carrier.

<3. Third Preferred Embodiment>

The inspecting device 100A according to the second preferred embodiment is constituted to detect, through the detector 132, the electromagnetic wave pulse LT1 radiated toward the light receiving surface 91S side. However, it is also possible to detect the electromagnetic wave pulse LT1 radiated onto the back side of the solar cell 90.

FIG. 13 is a diagram showing schematic structures of an irradiation part 12B and a detection part 13B in an inspecting device 100B according to a third preferred embodiment. Also in the inspecting device 100B, pulsed light LP1 emitted from a femtosecond laser 121 is divided into pulsed light LP11 and probe light LP12 through a beam splitter B1. Then, the pulsed light LP11 is incident vertically with respect to a light receiving surface 91S of a solar cell 90. Thereafter, any of electromagnetic wave pulses LT1 radiated (transmitted) from the solar cell 90 toward the back side of the solar cell 90 depending on the irradiation with the pulsed light LP11 is incident on a detector 132 through parabolic mirrors M1 and M2 or the like.

Also in the inspecting device 100B including the irradiation part 12B and the detection part 13B, it is possible to detect the electromagnetic wave pulse LT1 generated depending on the irradiation with the pulsed light LP11. Therefore, in the same manner as the inspecting device 100 according to the first preferred embodiment, the inspecting device 100B can inspect a characteristic of a photoexcited carrier generation region of the solar cell 90 in non-contact as greatly as possible. By the inspecting device 100B, similarly, it is possible to inspect a process for disappearance of the photoexcited carrier.

<4. Variant>

Although the preferred embodiments have been described above, the present invention is not restricted to the foregoing but various changes can be made.

For example, in the inspecting device 100 according to the preferred embodiment, the inspecting target is not restricted to the solar cell 90. The inspecting target of the inspecting device 100 may include a photo device (a photoelectric converter) for converting light containing visible light into current. As a photo device other than the solar cell, there is specifically assumed a photodiode or an image sensor such as a CMOS sensor or a CCD sensor. There is known an image sensor in which a light receiving element is formed in a portion serving as a back side of a substrate provided with a photo device in a usage state. By providing the substrate in the inspecting device 100 with a main surface on a light receiving side set to be a light receiving surface in the usage state, it is possible to detect a terahertz wave pulse well.

The respective structures described in the preferred embodiments and variant can be properly combined unless they are contradictory.

While the invention has been shown and described in detail, the foregoing description is in all aspects illustrative and not restrictive. It is therefore understood that numerous modifications and variations can be devised without departing from the scope of the invention.

What is claimed is:

1. An inspecting device for inspecting a photo device comprising:
    an irradiation part for irradiating said photo device with pulsed light;
    a detection part having a detector for detecting an electric field intensity of an electromagnetic wave pulse depending on irradiation with probe light emitted from a light source for said pulsed light;
    a delay part for changing a time difference between a time that said electromagnetic wave pulse arrives at said detector and a time that said probe light arrives at said detector, thereby delaying a timing for detecting said electromagnetic wave pulse through said detector;
    a temporal waveform restoration part for restoring a temporal waveform of said electromagnetic wave pulse based on said electric field intensity of said electromagnetic wave pulse detected by said detector in said plurality of pieces of detection timing;

an electromagnetic wave pulse analysis part for detecting a negative peak of said electric field intensity in said temporal waveform, and a setting part for setting a detection timing for detecting said electromagnetic wave pulse radiated from said photo device through said detector, based on the detection timing for detecting said negative peak in said temporal waveform.

2. The inspecting device according to claim 1, wherein said electromagnetic wave pulse analysis part detects two negative peaks of said electric field intensity in said temporal waveform and standardizes an electric field intensity of a second one of said two negative peaks which is detected later based on an electric field intensity of a first one of them which is detected earlier.

3. The inspecting device according to claim 2, further comprising:

a moving mechanism for relatively moving said photo device with respect to said irradiation part; and a control part for controlling said delay part, thereby changing said detection timing, said control part controlling said delay part in order to measure, in a predetermined measuring timing, an electromagnetic wave pulse to be radiated from each position of said photo device when irradiating said photo device with said pulsed light while moving said photo device relatively by means of said moving mechanism, and said measuring timing being determined based on a timing for detecting said two negative peaks in a temporal waveform of said electromagnetic wave pulse radiated depending on said irradiation with said pulsed light in a plurality of positions of said photo device in advance.

4. The inspecting device according to any one of claims 1 to 3, wherein said photo device constitutes a solar cell.

5. A method of inspecting a photo device comprising the steps of:

(a) irradiating said photo device with pulsed light;

(b) detecting, through a detector, an electric field intensity of an electromagnetic wave pulse to be radiated from said photo device in said step (a) depending on irradiation with probe light emitted from a light source for said pulsed light;

(c) changing a time difference between a time that said electromagnetic wave pulse arrives at said detector and a time that said probe light arrives at said detector in said step (b), thereby delaying a timing for detecting said electromagnetic wave pulse through said detector in said step (b);

(d) restoring a temporal waveform of said electromagnetic wave pulse based on said electric field intensity of said electromagnetic wave pulse detected in said plurality of pieces of detection timing in said step (b);

(e) detecting a negative peak of said electric field intensity in said temporal waveform restored in said step (d), and (f) setting a detection timing for detecting said electromagnetic wave pulse radiated from said photo device through said detector, based on the detection timing for detecting said negative peak in said temporal waveform.

* * * * *